United States Patent [19]

Shibata et al.

[11] Patent Number: 5,047,169
[45] Date of Patent: Sep. 10, 1991

[54] TOLANE COMPOUND

[75] Inventors: Toshihiro Shibata; Norio Kurosawa, both of Saitama, Japan

[73] Assignee: Adeka Argus Chemical Co., Ltd., Tokyo, Japan

[21] Appl. No.: 397,036

[22] Filed: Aug. 21, 1989

[30] Foreign Application Priority Data

Sep. 16, 1988 [JP] Japan .................................. 63-232997
Feb. 3, 1989 [JP] Japan ...................................... 1-26373

[51] Int. Cl.$^5$ ........................ C09K 19/06; C07C 41/00
[52] U.S. Cl. ............................ 252/299.6; 252/299.01; 568/631; 568/646
[58] Field of Search ..................... 252/299.01, 299.6; 568/631, 646

[56] References Cited

U.S. PATENT DOCUMENTS

| | | | |
|---|---|---|---|
| 3,925,482 | 12/1975 | Jacques | 252/299.01 |
| 3,928,399 | 12/1975 | Couttet et al. | 252/299.01 X |
| 3,976,591 | 8/1976 | Dubois et al. | 252/299.01 X |
| 4,528,114 | 7/1985 | Petrzilka | 252/299.6 |
| 4,705,870 | 11/1987 | Takatsu et al. | 252/299.6 X |
| 4,705,905 | 11/1987 | Takatsu et al. | 252/299.6 X |
| 4,713,468 | 12/1987 | Takatsu et al. | 252/299.6 X |
| 4,754,051 | 6/1988 | Sasaki et al. | 252/299.6 X |
| 4,814,516 | 3/1989 | Takeuchi et al. | 252/299.6 X |
| 4,820,878 | 4/1989 | Takatsu et al. | 252/299.6 X |
| 4,961,874 | 10/1990 | Takeuchi et al. | 252/299.6 |

FOREIGN PATENT DOCUMENTS

| | | | |
|---|---|---|---|
| 62-277333 | 12/1987 | Japan | 252/299.6 |
| 2-083346 | 3/1990 | Japan | 252/299.6 |
| 2-207056 | 8/1990 | Japan | 252/299.6 |

OTHER PUBLICATIONS

Demus, D. et al. Flussige Kristalle in Tabellen, VEB Deutscher Verlag fur Grundstoffindustrie, Leipzig, pp. 52–53, 1974, ibid pp. 104–107, 1984.

Primary Examiner—Robert L. Stoll
Assistant Examiner—Richard Treanor
Attorney, Agent, or Firm—Frishauf, Holtz, Goodman & Woodward

[57] ABSTRACT

A tolane compound represented by the following general formula (I) which can elevate the anisotropy ($\Delta n$) of the refractive index of a liquid crystal composition:

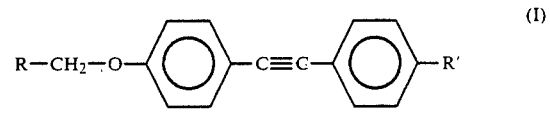

wherein R represents an alkynyl or an alkadienyl group having 3 to 18 carbon atoms, and R' represents an alkyl or an alkoxy group having 1 to 18 carbon atoms.

6 Claims, No Drawings

TOLANE COMPOUND

BACKGROUND OF THE INVENTION

1. Field of the Invention

This invention relates to a tolane compound which is useful as an electrooptical display material More particularly, it relates to an alkynyloxy or alkadienyloxytolane compound which is useful in elevating the anisotropy of the refractive index of an STN liquid crystal material when mixed with said liquid crystal material.

2. Description of the Prior Art

Recent development of STN liquid crystal cells shows a tendency toward black-and-white or full-colored ones, apart from conventional green or blue modes. Furthermore, it has been simultaneously attempted to develop a liquid crystal cell of high-speed response so as to satisfy the demand for animated images It is expected that the response rate of a STN liquid crystal cell can be elevated by reducing the thickness of the liquid crystal cell layer. In this case, however, the liquid crystal material to be charged into the cell should have a high anisotropy ($\Delta n$) of the refractive index. Although some tolane compounds having a relatively high $\Delta n$ have been proposed therefor, none of them has a sufficiently high $\Delta n$. Thus it has been urgently required to develop a tolane compound having a higher $\Delta n$.

SUMMARY OF THE INVENTION

Under these circumstances, the present inventors have conducted extensive studies in order to find out a compound which shows a high $\Delta n$ at a low viscosity. As a result, they have found that the addition of a novel tolane compound represented by the following general formula (I) to a liquid crystal material can significantly elevate the $\Delta n$ of said liquid crystal material.

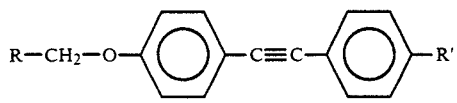

(I)

wherein R represents an alkynyl or an alkadienyl group having 3 to 18 carbon atoms, and R' represents an alkyl or an alkoxy group having 1 to 18 carbon atoms.

DETAILED DESCRIPTION OF THE INVENTION

Examples of the alkynyl group R in the compound of the present invention represented by the above general formula (I) include 1-propynyl, 1-butynyl, 2-butynyl, 1-pentynyl, 2-pentynyl, 1-hexynyl, 4-heptynyl, 6-octynyl, 6-nonynyl, 7-nonynyl, 8-undecynyl 10-tridecynyl and 12-pentadecynyl groups, while examples of the alkadienyl groups include 1,3-butadienyl and 1,6-heptadienyl groups.

Examples of the alkyl group R' in the formula (I) include methyl, ethyl, propyl, butyl, pentyl, hexyl, heptyl, octyl, nonyl, decyl, dodecyl, tridecyl, tetradecyl, hexadecyl and octadecyl groups, while examples of the alkoxy group include methoxy, ethoxy, propoxy, butoxy, pentyloxy, hexyloxy, heptyloxy, octyloxy, nonyloxy, decyloxy, dodecyloxy, tridecyloxy, tetradecyloxy, hexadecyloxy and octadecyloxy groups.

The compound represented by the above general formula (I) can be prepared by reacting an alcohol represented by the formula R—CH$_2$—OH with a 4-alkyl-4'-hydroxytolane.

The obtained alkynyloxytolane compound of the present invention can elevate the anisotropy of the refractive index of a STN liquid crystal material, when mixed with said liquid crystal material. Furthermore, the compound of the present invention is highly reactive, which makes it useful as an intermediate in the syntheses of various compounds. It is particularly useful as an intermediate in the preparation of an alkyltolane compound which is widely known as a liquid crystal compound.

To further illustrate the present invention, the following Examples will be given.

EXAMPLE 1

Synthesis of 4-n-propyl-4'-(2-butynyloxy)tolane

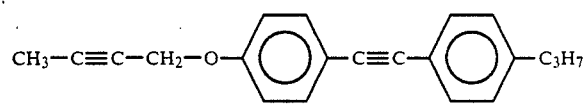

1.00 g of 4-n-propyl-4'-hydroxytolane, 0.35 g of 2-butyn-1-ol and 1.22 g of triphenylphosphine were dissolved in 10 ml of ether. Then 0.81 g of diethyl azodicarboxylate was added dropwise thereto. The mixture was stirred at room temperature for three hours. The triphenylphosphine oxide thus precipitated was filtered and the solvent was removed from the filtrate. The residue was purified by silica gel chromatography by using a mixture of n-hexane and diethyl ether (8:2) as a solvent and then recrystallized from n-hexane. Thus 0.67 g of white crystals (m.p.: 85.7° C.) were obtained.

The obtained product showed the following characteristic absorptions in infrared spectrometry, which indicated that it was the title compound.

2975 cm$^{-1}$, 1600 cm$^{-1}$, 1575 cm$^{-1}$, 1570 cm$^{-1}$, 1260 cm$^{-1}$, 1050 cm$^{-1}$ and 840 cm$^{-1}$.

EXAMPLE 2

Synthesis of 4-n-propyl-4'-(2-pentynyloxy)tolane

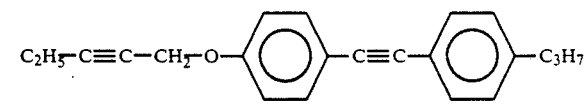

1.00 g of 4-n-propyl-4'-hydroxytolane, 0.42 g of 2-pentyn-1-ol and 1.22 g of triphenylphosphine were dissolved in 10 ml of ether. Then 0.81 g of diethyl azodicarboxylate was added dropwise thereto. The mixture was stirred at room temperature for three hours. Tne triphenylphosphine oxide thus precipitated was filtered and the solvent was removed from the filtrate. The residue was purified by silica gel chromatography by using a mixture of n-hexane and diethyl ether (8:2) as a solvent and then recrystallized from n-hexane. Thus 0.62 g of white crystals (m.p.: 67.8° C.) were obtained.

The obtained product showed the following characteristic absorptions in infrared spectrometry, which indicated that it was the title compound.

2975 cm$^{-1}$, 1600 cm$^{-1}$, 1575 cm$^{-1}$, 1570 cm$^{-1}$, 1260 cm$^{-1}$, 1050 cm$^{-1}$ and 840 cm$^{-1}$.

EXAMPLE 3

Synthesis of 4-n-heptyloxy-4'-(2,7-octadienyloxy)tolane

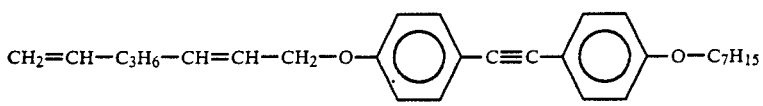

0.15 g of 4-n-heptyloxy-4'-hydroxytolane, 0.07 g of 2,7-octandien-1-ol and 0.16 g of triphenylphosphine were dissolved in 1.5 ml of ether. Then 0.12 g of diisopropyl azodicarboxylate was added dropwise thereto. The mixture was stirred at room temperature for 3.5 hours. The triphenylphosphine oxide thus precipitated was filtered and the solvent was removed from the filtrate. The residue was purified by silica gel chromatography by using a mixture of n-hexane and diethyl ether (95:5) as a solvent. Thus 0.19 g of a white powder (m.p.: 105.2°–106.1° C.) was obtained.

The obtained product showed the following characteristic absorptions in infrared spectrometry, which indicated that it was the title compound.

2925 cm$^{-1}$, 2855 cm$^{-1}$, 2550 cm$^{-1}$, 1610 cm$^{-1}$,
1515 cm$^{-1}$, 1285 cm$^{-1}$, 1245 cm$^{-1}$, 1005 cm$^{-1}$,
835 cm$^{-1}$ and 535 cm$^{-1}$.

EXAMPLE 4

Synthesis of 4-n-heptyloxy-4'-(2-butynyloxy)tolane

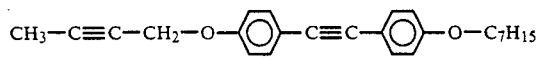

0.18 g of 4-n-heptyloxy-4'-hydroxytolane, 0.05 g of 2-butyn-1-ol and 0.19 g of triphenylphosphine were dissolved in 2.0 ml of ether. Then 0.15 g of diisopropyl azodicarboxylate was added dropwise thereto. The mixture was stirred at room temperature for 3.5 hours. The triphenylphosphine oxide thus precipitated was filtered and the solvent was removed from the filtrate. The residue was purified by silica gel chromatography by using a mixture of n-hexane and ethyl acetate (95:5) as a solvent. Thus 0.15 g of a white powder (m.p.: 115.0° C.) was obtained.

The obtained product showed the following characteristic absorptions in infrared spectrometry, which indicated that it was the title compound.

2975 cm$^{-1}$, 2850 cm$^{-1}$, 2250 cm$^{-1}$, 1605 cm$^{-1}$,
1515 cm$^{-1}$, 1280 cm$^{-1}$, 1240 cm$^{-1}$, 1000 cm$^{-1}$,
1000 cm$^{-1}$, 835 cm$^{-1}$ and 535 cm$^{1}$.

EXAMPLE 5

Synthesis of 4-n-heptyloxy-4'-(2-pentynyloxy)tolane

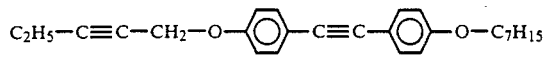

0.18 g of 4-n-heptyloxy-4'-hydroxytolane, 0.05 g of 2-pentyn-1-ol and 0.19 g of triphenylphosphine were dissolved in 2.0 ml of ether. Then 0.15 g of diethyl azodicarboxylate was added dropwise thereto. The mixture was stirred at room temperature for four hours. The triphenylphosphine oxide thus precipitated was filtered and the solvent was removed from the filtrate. The residue was purified by silica gel chromatography by using a mixture of n-hexane and diethyl ether (97:3) as a solvent. Thus 0.08 g of a white powder (m.p.: 98.7° C.) was obtained.

The obtained product showed the following characteristic absorptions in infrared spectrometry, which indicated that it was the title compound.

2950 cm$^{-1}$, 2875 cm$^{-1}$, 2250 cm$^{-1}$, 1610 cm$^{-1}$,
1520 cm$^{-1}$, 1380 cm$^{-1}$, 1245 cm$^{-1}$, 1010 cm$^{-1}$,
840 cm$^{-1}$ and 540 cm$^{-1}$.

EXAMPLE 6

Synthesis of 4-n-heptyloxy-4'-(3-hexynyloxy)tolane

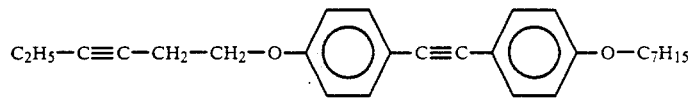

0.15 g of 4-n-heptyloxy-4'-hydroxytolane, 0.05 g of 2-hexyn-1-ol and 0.16 g of triphenylphosphine were dissolved in 2.0 ml of ether. Then 0.12 g of diisopropyl azodicarboxylate was added dropwise thereto. The mixture was stirred at room temperature for four hours. The triphenylphosphine oxide thus precipitated was filtered and the solvent was removed from the filtrate. The residue was purified by silica gel chromatography by using a mixture of n-hexane and diethyl ether (96:4) as a solvent. Thus 0.07 g of a white powder (m.p.: 68.8° C.) were obtained.

The obtained product showed the following characteristic absorptions in infrared spectrometry, which indicated that it was the title compound.

2950 cm$^{-1}$, 2875 cm$^{-1}$, 2300 cm$^{-1}$, 1615 cm$^{-1}$,
1520 cm$^{-1}$, 1290 cm$^{-1}$, 1255 cm$^{-1}$, 1050 cm$^{-1}$,
845 cm$^{-1}$, 830 cm$^{-1}$ and 540 cm$^{-1}$.

EXAMPLE 7

In order to prove that the addition of the tolane compound of the present invention to a liquid crystal material would elevate the Δn of said liquid crystal material, 10% of a tolane compound was added to a liquid crystal mixture comprising the following three compounds at a ratio of 1:1:1 and the change in the Δn of the liquid crystal mixture was monitored.

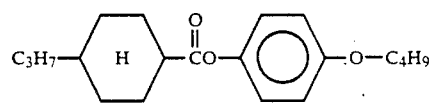

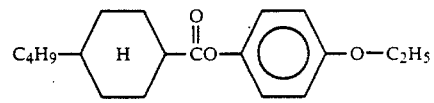

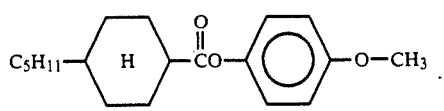

| Tolane compound | Δn |
| --- | --- |
| none | 0.085 |
| cpd. of Ex. 1 | 0.106 |
| cpd. of Ex. 2 | 0.102 |
| cpd. of Ex. 3 | 0.102 |
| cpd. of Ex. 4 | 0.109 |
| cpd. of Ex. 5 | 0.105 |
| cpd. of Ex. 6 | 0.104 |

These results indicate that the novel alkynyloxy or alkadienyloxytolane compound of the present invention would remarkably elevate the Δn of the matrix liquid crystals.

What is claimed is:

1. A tolane compound represented by the following general formula (I):

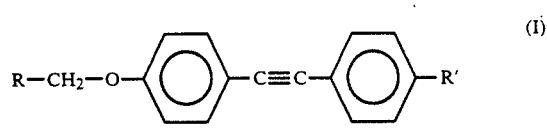

wherein R represents an alkynyl or an alkadienyl group having 3 to 18 carbon atoms, and R' represents an alkyl or an alkoxy group having 1 to 18 carbon atoms.

2. A tolane compound as claimed in claim 1, wherein R' is an alkyl group having 1 to 18 carbon atoms.

3. A tolane compound as claimed in claim 1, wherein R' is an alkoxy group having 1 to 18 carbon atoms.

4. A tolane compound as claimed in claim 1, wherein R is an alkynyl group having 3 to 18 carbon atoms.

5. A liquid crystal composition containing a tolane compound as claimed in claim 1.

6. A liquid crystal composition as claimed in claim 5 which comprises supertwisted nematic liquid crystals.

* * * * *